US006652456B2

(12) United States Patent
Gelfand et al.

(10) Patent No.: US 6,652,456 B2
(45) Date of Patent: Nov. 25, 2003

(54) MEDICAL SCREENING

(75) Inventors: Jeffrey A. Gelfand, Cambridge, MA (US); Timothy A. Brauns, Roslindale, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/731,101

(22) Filed: Dec. 6, 2000

(65) Prior Publication Data

US 2002/0068856 A1 Jun. 6, 2002

(51) Int. Cl.$^7$ .............................. A61B 5/00; G06K 9/00
(52) U.S. Cl. ........................ 600/300; 382/133; 128/920
(58) Field of Search ................................ 600/300–301, 600/407; 705/1–4; 382/133, 128; 345/665, 671; 356/372; 364/413.02; 128/903–904, 920–925; 435/4, 21; 702/19; 709/200, 100; 359/368; 707/104.1

(56) References Cited

U.S. PATENT DOCUMENTS 6,143,512 A  * 11/2000 Markovic et al. ............. 435/21
6,181,811 B1 *  1/2001 Kuan et al. ................. 382/133
6,226,392 B1 *  5/2001 Bacus et al. ................ 382/128

OTHER PUBLICATIONS

Bonin A, Service de Radiologie A, Groupe hospitalier Cochin, Paris: Teleimagerie medicale: Academie nationale de medicine (1999)—abstract—Medline.*
www.cytyc.com, Cytyc Corporation; ThinPrep® Pap Test (photographs from Cytyc Corporation, http://www.cytyc.com/85506Prd/prepady.htm).
www.tripathimaging.com/www.neopath.com, TriPath Imaging, Inc.; AutoCyte PREP and AutoPap® Guided Screening System.
Kavita N, McCrory DC, Myers ER, Bastian LA, Hasselblad V, Hickey JD, "Matchar DB. Accuracy of the Papanicolaou test in screening for and follow–up of cervical cytologic abnormalities: a systematic review", *Ann Int Med* 2000;132(10):810–819.
Michelow PM, Hlongwane NF, Leiman G., "Simulation of primary cervical cancer screening by the PAPNET system in an unscreened, high–risk community", *Acta Cytol* 1997;41(1):88–92.
Veneti S, Papaefthimiou M, Symiakaki H, Ioannidou–Mouzaka L., "PAPNET for cervical cytology screening: experience in Greece", *Acta Cytol* 1999;43(1):30–33.
Denny, et al., "Two–stage cervical cancer screening: an alternative for resource–poor settings", *Am J Obst Gyn* 2000; 183(2):383–388.
Godfrey SE, "The Pap smear, automated rescreening, and negligent nondisclosure", *Am J Clin Pathol* 1999; 111:14–17.
Sprenger E, Schwarzmann P, Kirkpatrick M., "The false–negative rate in cervical cytology: comparison of monolayers to conventional smears", *Acta Cytol* 1996;40:81–89.
AHCPR, Evaluation of cervical cytology. Summary, Evidence Report/Technology Assessment: No. 5. Agency for Health Care Policy and Research, Rockville, MD. Jan., 1999; http://www.ahrq.gov/clinic/cervsumm.htm.

(List continued on next page.)

*Primary Examiner*—Max F. Hindenburg
*Assistant Examiner*—Michael Astorino
(74) *Attorney, Agent, or Firm*—Fish & Richardson P.C.

(57) ABSTRACT

Mass medical, e.g., cervical cancer, screening is provided to areas of the world where a lack of sufficient laboratory infrastructure and technical skills presently compromises the effectiveness of screening or even makes mass screening impossible. These methods are cost-effective and provide excellent sensitivity and specificity in cervical cancer screening.

22 Claims, 3 Drawing Sheets

OTHER PUBLICATIONS

Nanda K, McCrory DC, Myers ER, Bastian LA, Hasselblad, V, Hickey JD, Matchar DB., "Accuracy of the Papanicolaou test in screening for and follow-up of cervical cytologic abnormalities: a systematic review", *Ann Int Med*2000;132(10):810–819.

Rosenthal DL, "Automation and the endangered future of the Pap test", *J Natl Cancer Inst* 1998;90:738–749.

Bartels PH, "Automation of primary screening for cervical cancer: sooner or later?" *Acta Cytol* 1999; 43(1):7–12.

Bartels PH, "Automated screening devices: expectations for the next generation", *Acta Cytologica* 200; 44(5):703–708.

Hutchinson ML, Agarwal P, Denault T, Berger B, Cibas ES., "A new look at cervical cytology: ThinPrep multicenter trial results",*Acta Cytol.* 1992; 36:499–504.

Aponte–Cipriani, et al., "Cervical smears prepared by an automated device versus the conventional method, a comparative analysis", *Acta Cytol.* 1995; 39:623–630.

Bishop JW, Gigner SH, Colgan TJ, et al., "Multicenter masked evaluation of AutoCyte PREP thin layers with matched conventional smears", *Acta Cytol* 1998;42:189–197.

Papillo JL, Zarka MA, St John TL., "Evaluation of the ThinPrep Pap test in clinical practice. A seven–month, 16,314—case experience in northern Vermont",*Acta Cytol.* 1998; 42:203–208.

Roberts JM, Gurley AM, Thurloe JK, Bowditch R, Laverty CR., "Evaluation of the ThinPrep Pap test as an adjunct to conventional Pap smear", *Med J Aust* 1997;167:466–469.

Mea, et al., "Image sampling in static telepathology for frozen section diagnosis", *J Clin Path* 1999;52(10):761–765.

Okada, et al., "Virtual microscopy" and the internet as telepathology consultation tools: diagnostic accuracy in evaluating melanocytic skin lesions, *Am J Dermatopath* 1999; 21(6):525–534.

Birdsong GG, "Automated screening of cervical cytology specimens" *Hum Pathol* 1996: 27(5):468–481.

Abulafia O, Sherer DM, "Automated cervical cytology: meta–analyses of the performance of the PAPNET system", *Obst Gynec Surv* 1999;54(4):253–264.

Bosanquet N, Coleman DV, Dore CJ, Douglas G, Magee JL, "Assessment of automated primary screening on PAPNET of cervical smears in the Prismatic trial", *Lancet* 1999;323(9162):1381–1385.

Brotzman GL, Kretzchmar S, Ferguson D, Gottlieb M, Stowe C., "Costs and outcomes of PAPNET secondary screening technology for cervical cytology: a community hospital's experience", *Ann Fam Med* 1999; 8(1):52–55.

Brown AD, Garber AM., "Cost–effectiveness of 3 methods to enhance the sensitivity of Papanicolaou testing", *Obst Gynec Surv* 1999; 54(5):305–306.

Dunton C., "New technology in Papanicolaou smear processing", *Clin Obstet Gynec* 2000; 43(2):410–417.

Howell LP, Belk T, Agdoigs R, Davis R, Lowe J., "AutoCyte Interactive Screening Sytem: experience at a University hospital cytology laboratory",*Acta Cytol* 1999;43(1):53–64.

O'Leary TJ, Tellado M, Buckner SB, Ali IS, Stevens A, Ollayos C., "PAPNET–assisted rescreening of cervical smears: cost and accuracy compared with a 100% manual rescreening strategy", *JAMA* 1998; 279(3):235–237.

* cited by examiner

MEDICAL SCREENING

TECHNICAL FIELD

This invention relates to medical screening.

BACKGROUND

Various medical conditions are the subject of routine screening of populations of patients who are potential candidates for the particular condition. For example, in the United States women are routinely screened for cervical cancer.

Carcinoma of the cervix is one of the most common malignancies in women. Worldwide, an estimated 470,000 women develop cervical cancer each year, with more than 80% of these cancers occurring in the developing world. In general, cervical cancer progresses slowly through several well-defined stages, and thus early detection permits the cancerous lesions to be treated with nearly 100% success. The initiation of mass screening has reduced cervical cancer mortality in the United States by 50% over the last 30 years (Kavita, et al., *Accuracy of the Papanicolaou test in screening for and follow-up of cervical cytologic abnormalities: a systematic review. Ann Int Med* 2000; 132(10):810–819). However, many countries lack the medical infrastructure or technical expertise to carry out effective mass screening (Michelow, et al., *Simulation of primary cervical cancer screening by the PAPNET system in an unscreened, high-risk community. Acta Cytol* 1997; 41(1):88–92; Veneti, et al., *PAPNET for cervical cytology screening: experience in Greece. Acta Cytol* 1999; 43(1):30–33; Denny, et al., *Two-stage cervical cancer screening: an alternative for resource-poor settings. Am J Obst Gyn* 2000;183(2):383–388). As a result, cervical cancer is the leading cancer-related cause of death in women of the developing world. (Denny, et al., supra).

The standard method of cervical cancer screening uses the Pap smear, named after Dr. George Papanicolaou, who introduced it into clinical practice in the 1930s. Pap smear screening is presently a two-step process of collection and inspection. First, a physician or other trained medical professional collects a sample of cells from the cervix of the patient using an ectocervical spatula, an endocervical brush, and/or cotton swabs. Once collected, the specimen is processed by placing a portion of the sample on a dry glass slide, fixing it with a preservative, placing a cover slide on the sample, and staining it. Once the slide has been prepared and stained, it is manually screened by a cytotechnologist, under a microscope, for potentially abnormal cells. Suspicious cells may be further examined by a cytopathologist. Once a determination of the status of the sample is made, a report is produced that is normally sent to the referring physician or clinic.

There are inherent limitations in this standard screening approach related to the quality of the sample, the quality of the slide, and the effectiveness of the screener. The standard technique of placing the sampling spatula or brush on the glass slide results in capture of only the cells that are in contact with the slide. There is generally no proportional representation on the slide of all the cells taken from the cervix. In some cases, an inadequate number of cells are preserved on the slide, resulting in the need for re-screening. Even when the number of cells is adequate, the appearance of the resultant slide can be highly variable. The cells may be clumped, overlapping, and poorly preserved. Visibility may be partially obscured by blood, inflammation or drying artifacts.

There are several factors that limit the effectiveness of the slide screener. First, a typical Pap smear slide contains up to 300,000 cells. With a limited amount of time to screen each slide, the screener cannot examine each cell, but instead must do a quick overall scan of the slide and then sample the most promising areas at greater magnification looking for abnormal cells. Second, the screener must cope with habituation (the expectation of a negative result) and fatigue.

These limitations affect both the sensitivity and specificity of testing. Sensitivity refers to the proportion of cellular abnormalities that are actually detected. Sensitive tests reduce the number of false negatives—slides reported as being within normal limits when, in reality, there were cells indicative of abnormal changes. Specificity refers to the proportion of normal slides that are actually reported as normal. Specific tests have a low rate of false positives—reports of findings that require follow-up when, in fact, the smear was normal.

While the upper limit of sensitivity in Pap smear screening is 95% due to inherent sampling error (Godfrey S E, *The Pap smear, automated rescreening and negligent nondisclosure. Am J Clin Pathol* 1999; 111:14–17), the actual sensitivity rate for standard screening ranges from 30–93% in the United States, with the specificity of standard screening at between 86–100% (Sprenger, et al., *The false-negative rate in cervical cytology: comparison of monolayers to conventional smears. Acta Cytol* 1996;40:81–89; AHCPR, Evaluation of cervical cytology. *Summary, Evidence Report/Technology Assessment: Number 5.* Agency for Health Care Policy and Research, Rockville, Md. January 1999. http://www.ahrq.gov/clinic/cervsumm.htm.; Nanda, et al., *Accuracy of the Papanicolaou test in screening for and follow-up of cervical cytologic abnormalities: a systematic review. Ann Int Med* 2000;132(10):810–819). There is little information on quality control and therefore sensitivity outside the United States, Canada and Europe.

In addition to these technical aspects, conducting standard, manual cervical cancer screening requires a sufficient quantity of qualified cytotechnologists and cytopathologists. This quantity will determine the volume of Pap smear slides that can reasonably be screened by such trained personnel. While the Clinical Laboratory Improvement Amendment of 1988 limits the number of slides that can be reviewed in an eight-hour day to 100, such a level of productivity is highly unlikely (Rosenthal D L, *Automation and the endangered future of the Pap test. J Natl Cancer Inst* 1998; 90:738–749.) A more reasonable optimal number is 60 per day, while an average would be 40–50. This translates into an individual cytotechnologist having the capacity to screen 10,000–14,000 slides per year. In the United States there are approximately 4,800 certified cytotechnologists. Although there is presently a slight shortage of qualified personnel in this field, this is an adequate number to screen the 50–60 million Pap smears done every year.

However, many areas of the world lack qualified and adequately trained cytotechnologists and cytopathologists. This shortage is often a result of the lack of training infrastructure and the low reimbursement rate for such screening tests (Bartels P H. *Automation of primary screening for cervical cancer: sooner or later? Acta Cytol* 1999; 43(1):7–12.) Such a situation makes it unlikely that women at risk will have adequate access to screening, or any access at all.

An example of a country in which there is such a lack of qualified cytotechnologists and cytopathologists is the United Arab Emirates. The total population of the United Arab Emirates (UAE) is approximately four million people. To screen one-third of the adult women of this country (representative of screening of every woman of screenable age once every three years) roughly 300,000 Pap smears per year would need to be done. The standard screening method would require 20–30 cytotechnologists doing nothing but Pap smears. Presently there are 15 hospitals and 15 clinical laboratories in the UAE. There are only 44 M.D. pathologists in the entire country, and very few of these are likely to be cytopathologists. While exact figures are lacking, it is reasonable to assume that, at most, only half of the hospitals and laboratories have even one cytotechnologist. Based on this assumption, at most, the UAE possesses a maximum of 15 cytology technicians. This assumption is supported by the fact that very few Pap smears are presently done in the United Arab Emirates. It is clear that this country does not have the qualified technical people to accommodate all the women who would need to be tested if population screening were to be performed. In addition, new laboratory infrastructure, including cytotechnologist workstations and equipment would also need to be created.

SUMMARY

The inventors have developed new methods for providing medical screening, for example cervical cancer screening. In the case of cervical cancer screening, these methods provide excellent sensitivity and specificity in cervical cancer screening, and provide a cost-effective way of delivering mass cervical screening to areas of the world where a lack of sufficient laboratory infrastructure and technical skills presently compromises the effectiveness of screening or even makes mass screening impossible. It is thus hoped that these methods will significantly impact the rate of cervical cancer deaths in developing countries.

Methods of the invention separate cervical cancer screening task into two major segments: (1) sampling, slide preparation and an initial screening of slides, all of which are done by automation at a first geographic location (typically locally in a developing country); and (2) detailed reading of suspicious cells and report generation, which is performed by human experts at a second geographic location (typically at a remote site in a country that has adequate technical expertise). The first segment is supported by a highly automated system that provides a high quality slide and an automated, first-pass identification and elimination of normal smears, without requiring a highly trained technical staff. The second segment takes place at a remote site where highly-trained cytotechnologists and expert cytopathologists receive Internet-based, high-resolution digital images of suspicious cells or cell clusters, provide interpretation of results, and create reports based on these findings.

The great advantage of this segmented screening approach is that the expertise of medical institutions in industrialized countries can be brought to bear on samples from geographic areas that lack technical proficiency, or in which it is prohibitively expensive to recruit and maintain qualified medical personnel.

In some implementations, workflow and reporting is integrated through an Internet-based communication system and an automated messaging system.

Broadly, the invention features a method of providing a medical interpretation of each of a number of images associated respectively with different patients, including: (a) in a first geographic location, automatically screening diagnostic test data associated with the patients to screen out test data for which the medical interpretation is negative, and automatically producing digital images associated with test data that is likely to be indicative of abnormality, (b) transmitting the digital images electronically to a second geographic location, the medical interpretation for these digital images being possibly positive; (c) at the second geographic location, presenting the digital images to an experienced person to evaluate the images and confirm or reject the possibly positive medical interpretation; and (d) returning the medical interpretation electronically to the first geographic location. The first geographic location is one in which the automatic screening is legally permitted to be done as part of a medical diagnosis, and in which the number of experienced people capable of generating the medical interpretation as a ratio of the population needing screening is lower than in the second geographic location.

In one aspect, the invention features a method of providing a medical interpretation of each of a number of Pap smear slides, each slide including cellular material. The method includes: (a) in a first geographic location, automatically screening the Pap smear slides to screen out slides for which the medical interpretation is negative and automatically processing the remaining slides to produce digital images of cellular features that are likely to be indicative of abnormality; (b) transmitting the digital images electronically to a second geographic location, the medical interpretation for these digital images being possibly positive; (c) at the second geographic location, presenting the digital images to an experienced person to evaluate the images and confirm or reject the possibly positive medical interpretation; and (d) returning the medical interpretation electronically to the first geographic location. The first geographic location is one in which the automatic screening is legally permitted to be done as part of a medical diagnosis, and in which the number of experienced people capable of generating the medical interpretation as a ratio of the population needing screening is lower than in the second geographic location.

Implementations of this aspect of the invention may include one or more of the following features. The first geographic location is a developing country. The second geographic location is an industrialized country. Each raw image data file includes images of cells, and the method further includes, prior to electronic transmission of the remaining files, processing the remaining files to select for transmission images of cells which are most likely to result in a positive medical interpretation. The experienced person is a cytotechnologist or cytopathologist. The transmitting and returning steps are performed via the Internet, or, alternatively, by email. The method further includes preparing the Pap smears using a liquid-based thin-film sample preparation process, e.g., using an automated system. High volumes of Pap smears are processed at a low cost. The remaining files (the files that are manually reviewed) represent less than about 50% of the Pap smears.

In another aspect, the invention features a method for providing a medical interpretation for cervical cancer including: (a) receiving, at a second geographic location, an electronic transmission of a file from a first location, the file including information identifying a patient and images of cells sampled from the cervix of the patient, the file having been automatically screened, prior to transmission, so that the file is only transmitted if it contains cells for which the medical interpretation is possibly positive, (b) generating a medical interpretation of the images, the generating step being performed by an experienced person, and (c) transmitting the medical interpretation electronically to the first geographic location. The first geographic location is one in which the number of experienced people capable of generating the medical interpretation as a ratio of the population needing screening is lower than in the second geographic location, and in which the automatic screening is legally permitted to be done as part of a medical diagnosis.

The invention also features a method of providing a medical interpretation of each of a number of Pap smears, by utilizing the facilities at a remote geographic location, including: (a) in a first geographic location, automatically screening the Pap smear slides to screen out slides for which the medical interpretation is negative, and automatically processing the remaining slides to produce digital images of cellular features that are likely to be indicative of abnormality, (b) transmitting the digital images electronically to the remote geographic location for medical interpretation, the medical interpretation for these digital images being possibly positive, and (c) receiving the medical interpretation electronically from the remote geographic location. The first geographic location is one in which the automatic screening is legally permitted to be done as part of a medical diagnosis, and in which the number of experienced people capable of generating the medical interpretation as a ratio of the population needing screening is lower than in the remote geographic location.

Other features and advantages of the invention will be apparent from the description and drawings, and from the claims.

DETAILED DESCRIPTION

Figure 1:
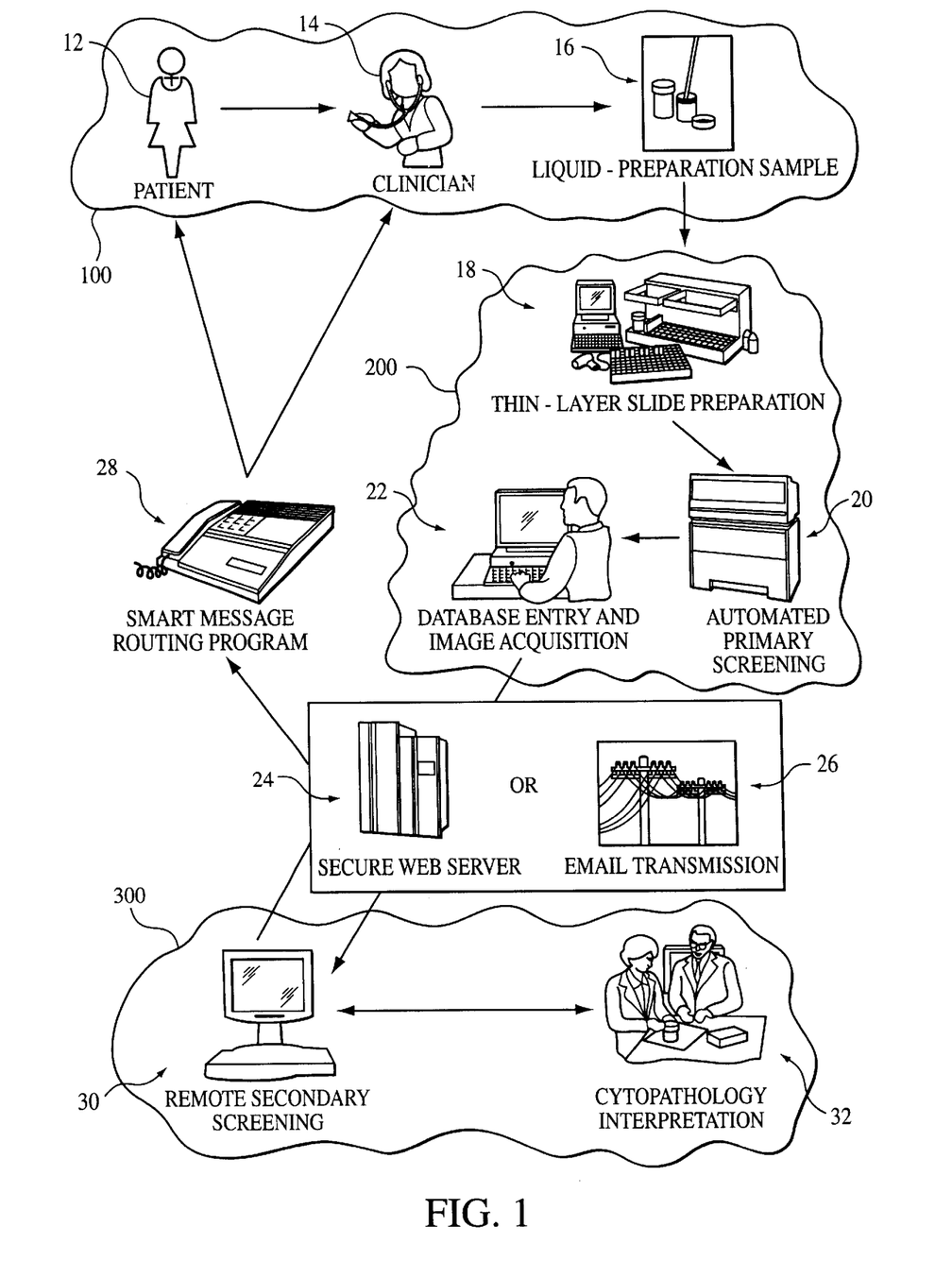
FIG. 1 is a diagrammatic representation of a method according to one aspect of the invention.

A cervical screening method of the invention is shown schematically in FIG. 1. The steps of this method will first be described generally, with reference to FIG. 1, after which each step will be described in further detail.

According to this method, a patient (12) visits a clinician (14), who obtains a sample of cervical cells using standard methods. The patient and clinician are located in a first geographic location (100), typically in which there is a shortage of trained medical personnel and/or laboratory infrastructure relative to the population in need of Pap screening. An example of such a location is the United Arab Emirates. The clinician then fixes the sample using liquid preparation techniques (16), as will be described in detail below, and sends the sample to a laboratory that has facilities for thin-layer slide preparation.

At the laboratory, a slide is automatically prepared using thin-layer techniques (18). The slide is then subjected to an initial automated primary screening (20), which determines whether the slide meets a predetermined standard and can be classified as "within normal limits," or whether the slide possibly contains abnormal cells that require further evaluation. Images and textual information from this automated primary screening are entered into a database (22), in a file that is identified with the patient's name and other personal information. Steps (18)–(22) is performed at a location (200), which may be at or near the first geographic location (100), at or near the second geographic location (300), discussed below, or at yet another geographic location.

If the file is classified as being within normal limits, this information is transmitted to the patient and/or clinician over the Internet (24) or via email (26), using a smart message routing program (28). In this case, this information is the final medical interpretation of the patient's slide. If, on the other hand, the file is identified as requiring further evaluation, selected images of potentially abnormal cells on the slide are transferred, over the Internet (24) or by email (26), to a remote secondary screening facility (30) at a second geographic region (300). The remote screening facility may be in a geographic region where there is a surplus of available trained medical personnel and/or laboratory infrastructure relative to the population in need of Pap screening. The cells are then evaluated at the secondary screening facility by a cytotechnologist, and, if necessary, by a cytopathologist (32), to obtain a medical interpretation. This medical interpretation is then transmitted to the patient and/or clinician over the Internet or via email.

Sample Collection Using Liquid-Based, Thin-Layer Smear Preparation Kits

In place of the standard method of collecting a Pap smear, cell samples are collected using existing liquid-based, smear preparation kits. As in the standard method, the clinician gathers the Pap smear using a broom-type cytobrush or an endocervical brush and plastic spatula. However, instead of smearing this on the slide, the cell sample is rinsed into a bottle of liquid fixative. The sampling instruments are then discarded and the bottle is sealed, labeled, and sent to a laboratory for processing.

This technique produces a suspension of uniformly dispersed cells. The liquid provides long-term preservation of the cells, and the quick transfer from the cervix to the bottle prevents artifacts of drying that are often present on manually prepared slides. The fixative also lyses any red blood cells that are present (these are not important to the screening test). There is a very short learning curve associated with this liquid-based technique. Such liquid-preparation systems are currently produced by Cytyc Corporation (THINPREP® Pap Test™) and TriPath Imaging, Inc. (as part of the AUTOCYTE® PREP system).

Slide Preparation Using Automated Techniques

Traditional slide preparation involves the clinician placing a portion of the smear on a slide, fixing, covering, and staining it. In the present method, this approach is replaced with an automated system that takes the liquid-based sample described above and prepares a slide. Suitable automated systems include the THINPREP® 2000 and 3000 processors (Cytyc Corporation, referred to herein as "the THINPREP® system") and the AUTOCYTE® PREP System (TriPath Imaging, Inc., referred to herein as "the PREP system").

At a designated laboratory (generally in the same country or geographic region as the clinic where samples are taken), the liquid sample is placed in the automated system (e.g., the THINPREP® or PREP system). First, a gentle dispersion step breaks up blood, mucous and other non-diagnostic material in the sample. This step also thoroughly mixes the sample so there is a uniform distribution of cells throughout the suspension. The PREP system also includes a centrifugation step to separate epithelial cells from the other material.

In the THINPREP® system, the sample is drawn through a filter that collects a thin layer of cellular material. Sensors monitor flow rates to ensure that the density of the cells deposited on the slide is not too great or too small. Once the desired density is reached, the filtration process stops. The cells on the filter are then transferred to a glass slide using computer controlled mechanical positioning and positive air pressure. The PREP system works slightly differently, utilizing density-gradient centrifugation to separate the epithelial cells, and then depositing the cells on the slide by gravity.

Once the sample is deposited, the slide is then fixed and stained automatically. These automated systems also produce a uniform field size (approximately 20 mm for THIN-PREP® slides, and 13 mm for the AUTOCYTE® PREP system).

Figure 2:
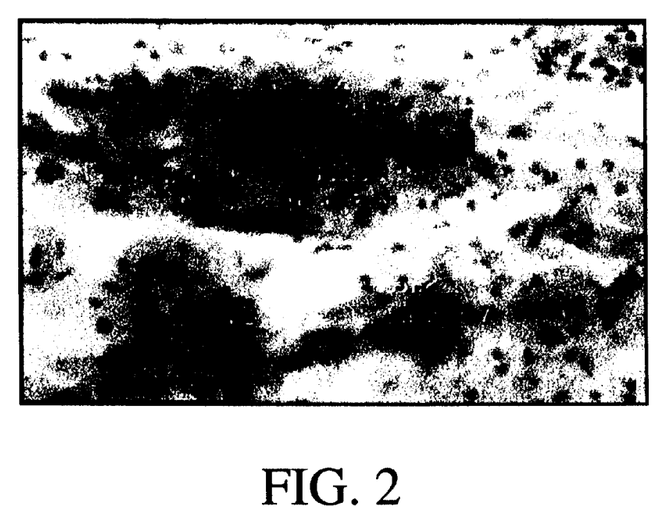
FIGS. 2 and 2A are magnified images of a standard Pap smear specimen and a liquid-based, thin-layer sample preparation, respectively (photographs from Cytyc Corporation, http://www.cytyc.com/85506Prd/prepady.htm).
Figure 2A:
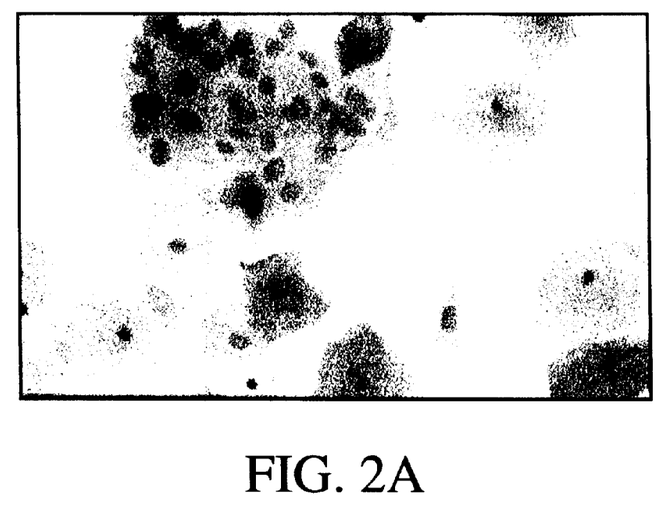

This automated slide-preparation process limits the need for highly trained technicians. In most cases, the operator simply loads a sample, slide and filter and pushes "start;" the software takes over and signals when the slide is ready. The automated process also results in an improved slide sample. FIGS. 2 and 2A show the difference between a standard Pap smear preparation and a liquid-based, thin-layer preparation. In the liquid-based preparation, non-diagnostic organic materials that can obscure the view of cells of interest are removed. The automated system deposits a proportionate and representative sample of all the cells from the original smear. A smaller number of cells (approximately 40,000–70,000) are deposited in a single layer, and most of the clumping of cells found in standard slides is eliminated. Inflammatory cells and blood cells are also eliminated from the sample.

The result is a superior presentation of a representative sample of epithelial cells. A number of clinical studies show that these automated systems are more sensitive than conventional smears while achieving comparable specificity (Hutchinson, et al., *A new look at cervical cytology: Thin-Prep multicenter trial results. Acta Cytol.* 1992; 36:499–504; Aponte-Cipriani, et al., *Cervical smears prepared by an automated device versus the conventional method, a comparative analysis. Acta Cytol.* 1995; 39:623–630; Bishop, et al., *Multicenter masked evaluation of AutoCyte PREP thin layers with matched conventional smears. Acta Cytol* 1998; 42:189–197; Papillo, et al., *Evaluation of the ThinPrep Pap test in clinical practice, a seven-month, 16,314-case experience in northern Vermont. Acta Cytol.* 1998; 42:203–208). Both raise sensitivity to over 90% and decrease the number of unsatisfactory slides (Roberts, et al., *Evaluation of the ThinPrep Pap test as an adjunct to conventional Pap smear. Med J Aust* 1997;167:466–469; Bishop, et al., supra). In addition, the greater clarity in the sample lowers the number of ASCUS (atypical squamous cells of undetermined significance) diagnoses, allowing the slide to be placed in either a benign or potentially premalignant category (Rosenthal, supra).

Automated Slide Scanning and Digital Imaging

In this step, automated screening of the slide replaces the traditional manual review. Central to this step is the use of a screening machine that is able to scan the slide, evaluate the slide for potential abnormalities, and capture high-power digital images of cells or cell clusters that require further review by a cytotechnologist. Suitable screening machines have the following components: (1) an automated loading and sorting system that can handle multiple slides at the same time; (2) an automated, high speed scanning microscope; (3) a software program that identifies the slide with patient identification data; (4) software that works with the scanning microscope to numerically rank the likelihood of the slide to be abnormal based on the assessment of cells sampled in the assessment pass; (5) a digital camera that can take photographs of cells or cell clusters at high magnification; and (6) a hardware/software system to provide output of these digital images to high-resolution monitors and/or servers. The AUTOPAP® GS system, manufactured by Tripath Imaging, Inc., is capable of providing most of this functionality, but it does not presently upload these images to a database system. A simple modification of the system is required to add a digital camera that ports selected images into an image management database.

On a connected PC or terminal emulator that interfaces with the screening machine, the operator enters information about the slide to be read, including demographic information on the patient and contact information regarding the clinician. A bar code is then printed out and placed on the slide. The operator will take the coded slides and load them into the screening machine. This patient information is also imported into an image management database that creates a patient profile, contains a system of tracking the status of the screening for that patient, enables digital microscopic images to be linked to a patient profile, and produces standard reports. The AUTOCYTE® Image Management System, commercially available from TriPath Imaging, Inc., is an example of this type of database.

The screening machine performs a scanning pass of each slide at low power. During this scan, multiple software algorithms are run against the cells on the slide. Object classification algorithms process each acquired image and assign a classification to each of the detected objects in the image. There may be multiple algorithm programs operating independently to provide redundant assessment. The results of the object classification from each image are then compiled, and another algorithm assesses the number and distribution of the classification objects. Based on this assessment, the slide is given a score to reflect the number and degree of abnormal cells. These classification routines allow a slide to be classified as "within normal limits" based on the object classification score for the slide. These "normal" slides are not subjected to further automated processing.

A report is immediately generated in the database for each of the normal slides. Off-the-shelf interactive, intelligent message routing software (referred to elsewhere herein as "smart message routing" software) provides automated reporting of these results. Suitable smart message routing software is commercially available, e.g., from The Method Factory, Inc. (Cambridge, Mass.). Such a system monitors the database for status changes in results. When a final result is reported, the software takes the diagnostic report text and transmits the results to the recipients listed on the image management database described above. The smart messaging system can transmit these results by email, by fax, or by regular mail.

Figure 3:
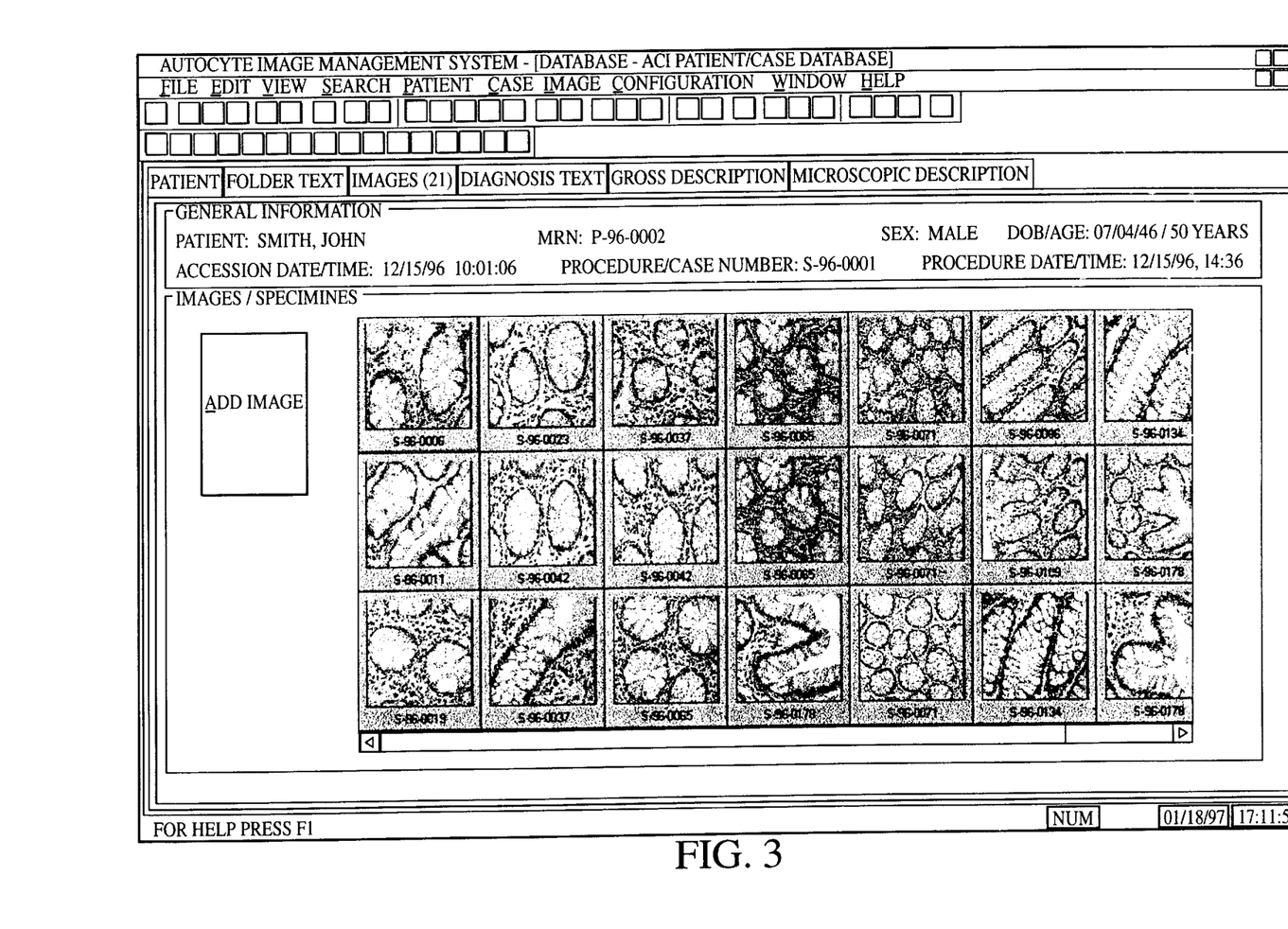
FIG. 3 is a screenshot from AUTOCYTE® Image Management System (TriPath Imaging, Inc.).

For the remaining slides not classified as "within normal limits," the system identifies a large number of the objects identified as "most abnormal" from each object classification algorithm. Typically, the top 60–64 images are selected from each independent algorithm, resulting in a total of 120–128 images. The locations of these cells or cell clusters are stored by the system for subsequent review. The scanner then switches to a high-power microscope lens and captures images of these cells using a digital camera. These high-power images are combined with low-power overview images of the entire slide and are coupled with the patient identification information. This "file" is ready for output to the image management software. Images are converted to a Joint Photographers Experts Group (JPEG) format, which permits compression of images with minimal loss of useful visual information. Compression ratios of no more than 20:1 are used to prevent degradation of image quality that would affect ability to perform readings on the images (Mea, et al., *Image sampling in static telepathology for frozen section diagnosis. J Clin Path* 1999; 52(10):761–765; Okada, et al., "Virtual microscopy" and the internet as telepathology consultation tools: diagnostic accuracy in evaluating melanocytic skin lesions. *Am J Dermatopath* 1999; 21(6): 525–534). FIG. 3 shows an example of an electronic folder containing thumbnail versions of stored JPEG cytology images.

Thus, the slides are screened using computer algorithms to weed out or remove from transmission, at the site of robotic processing, all images judged by computer algorithm to be normal. Therefore, for the 25–50% of smears meeting a preset standard as "within normal limits," the images are not forwarded on to distant experts—that is, primary screening is done robotically. For the remaining slides marked for subsequent review at the remote site, only those images from each individual slide viewed as most suspicious are transmitted. Thus, from approximately 50,000 cells on the slide, only the most "abnormal" 120 cells would be captured for transmission. If desired for ongoing quality control, an additional 10% of all smears would be forwarded for expert review.

At present, a few automated screening machines have received FDA approval for use in the United States. One of these, The AUTOPAP® 300 CQ system (TriPath Imaging, Inc.) is approved for use in both primary and quality control screening. It removes 25% of all samples from manual review. Some machines, like the PAPNET® system, are only approved for quality control rescreening. Other devices, like the AUTOPAP® GS system and the AUTOCYTE® SCREEN system, have not been approved for use in the United States, but are in use in Europe and Asia. To the extent that automated screening is approved for use in North America now and in the future, the screening methods of the invention can be used to provide cervical cancer screening to areas in North America that are lacking in qualified medical personnel and/or laboratory infrastructure, such as rural areas.

Secure Internet Transmission/Storage of Digital Images

This step geographically separates the initial screening of Pap smear slides from the evaluation of the particular cell images selected by the scanning system. The cell images from slides requiring review are transmitted to a site, remote from the point of sample acquisition and initial screening, where trained cytotechnologists and cytopathologists perform a manual review. This transfer may be accomplished using one of the following methods. In a first method, the folder with the JPEG images is transmitted by email using encryption security software. Files are already stored in the image management software database. These files are attached to email (standard Multipurpose Internet Mail Extension—MIME—protocol) and sent utilizing a commercially available encryption technology, such as NETWORK ASSOCIATES® PGP system. This system will be able to utilize a variety of bandwidth connections to the Internet, including 56 K, ISDN, or cable modem connections. Since screening does not require "near real time" processing, files may be batched for transmission at the end of each business day.

A second method involves placement of the image management database on a web-based server. Personnel at the sampling site log into the database utilizing a web browser, such as MICROSOFT INTERNET EXPLORER® web browser or NETSCAPE COMMUNICATOR® web browser. The server can be located at their local site, at the remote reading site, or at some other site. Access to the database would be protected by standard security protocols. After logging in and creating the patient profile, images from the automatic scanner are uploaded to the patient file. The patient file is then flagged as requiring review. Connections can be made to the server by high-speed ISDN, DSL, cable or T1 connections.

Remote Reading and Reporting of Digital Images

The secondary screening, i.e., the review of the 120–128 images from each slide selected by the automated screening system, takes place at a site remote from the sample robotic processor/screener. This model allows the secondary screening to be performed in a geographic area where it is relatively easy to maintain a technical staff with sufficient expertise and experience to provide quality screening. Suitable sites for secondary screening would include large hospitals in industrialized countries, for example Massachusetts General Hospital or the Brigham and Women's Hospital, in the United States.

Remote secondary screening consists of three stages. First, a cytotechnologist screens all the images sent with each slide, and classifies each image set as either "not needing further review" or "needing further review." The screening is done on a standard workstation with a large, high-resolution video monitor. The workstation software supports both the encrypted email system and the web-based database, and has software to support the viewing of the images contained in each patient folder.

For image sets requiring further review, the cytotechnologist identifies the specific images within the set that require further review, and passes these on to a cytopathologist, who provides a diagnostic reading. In a small number of cases, actual review of the slide is required. The cytopathologist then requests the actual Pap smear slide (i.e., the liquid-based, thin-film slide described above) to be sent by express mail.

Once the secondary screening is complete, the cytotechnologist or cytopathologist enters diagnostic text into the database and changes the sign out status of the patient folder to "completed." If the email system is used, the folder is then emailed back to the local site by encrypted transmission. If the web-based system is used, local staff will be able to check the database for completed readings. "Smart message routing" software handles automated results reporting.

Advantageously, secondary screening of the selected images is up to five times faster than standard screening (Birdsong G G. *Automated screening of cervical cytology specimens. Hum Pathol* 1996: 27(5):468–481; Rosenthal, supra).

Other embodiments are within the claims.

What is claimed is:

1. A method comprising
   in a first geographic location, automatically screening diagnostic data associated with patients to screen out data for which a medical interpretation is negative, and automatically producing digital images associated with data as to which there are possibly positive medical interpretations;
   the first geographic location being one in which the automatic screening is permitted to be done as part of a medical diagnosis;

transmitting the digital images electronically to a second geographic location;

at the second geographic location, presenting the digital images to an experienced person to provide evaluations of the possibly positive medical interpretations; and returning the evaluations electronically to the first geographic location;

the first geographic location being one in which a ratio of experienced people capable of providing the evaluations to a population needing screening is lower than in the second geographic location.

2. A method comprising:

in a first geographic location, automatically screening Pap smear slides to screen out slides for which a medical interpretation is negative and automatically processing the remaining slides to produce digital images of cellular features as to which there are possibly positive medical interpretations;

the first geographic location being one in which the automatic screening is permitted to be done as part of a medical diagnosis;

transmitting the digital images electronically to a second geographic location;

at the second geographic location, presenting the digital images to an experienced person to provide evaluations of the possibly positive medical interpretations; and returning the evaluations electronically to the first geographic location;

the first geographic location being one in which a ratio of experienced people capable of providing the evaluations to a population needing screening is lower than in the second geographic location.

3. The method of claim 1 or 2 wherein the first geographic location comprises a developing country.

4. The method of claim 1 or 2 wherein the second geographic location comprises an industrialized country.

5. The method of claim 2 wherein the experienced person comprises a cytotechnologist or cytopathologist.

6. The method of claim 1 or 2 wherein the transmitting and returning steps are performed via the Internet.

7. The method of claim 1 or 2 wherein the transmitting and returning steps are performed via email.

8. The method of claim 2 further comprising preparing the Pap smears using a liquid-based thin-film sample preparation process.

9. The method of claim 8 wherein the preparing step is performed using an automated system.

10. The method of claim 2 wherein the remaining slides represent less than about 50% of the Pap smear slides.

11. A method comprising receiving, at a second geographic location, an electronic transmission of a file from a first location, the file including information identifying a patient and images of cells sampled from the cervix of the patient, the file having been automatically screened, prior to transmission, so that the file is only transmitted if it contains cells as to which there are possibly positive medical interpretations, the first geographic location being one in which the automatic screening is permitted to be done as part of a medical diagnosis, providing an evaluation of the images, the generating step being performed by an experienced person, and the first geographic location being one in which a ratio of experienced people capable of providing the evaluation to a population needing screening is lower than in the second geographic location, and transmitting the evaluation electronically to the first geographic location.

12. The method of claim 11 wherein the experienced person comprises a cytotechnologist or cytopathologist.

13. The method of claim 11 wherein the transmitting step is performed via the Internet.

14. The method of claim 11 wherein the transmitting step is performed via email.

15. A method of providing a medical interpretation of each of a number of Pap smears, by utilizing the facilities at a remote geographic location, comprising in a first geographic location, automatically screening the Pap smear slides to screen out slides for which the medical interpretation is negative, and automatically processing the remaining slides to produce digital images of cellular features that are likely to be indicative of abnormality, the first geographic location being one in which the automatic screening is permitted to be done as part of a medical diagnosis, transmitting the digital images electronically to the remote geographic location for evaluation, and receiving the evaluation electronically from the remote geographic location, the first geographic location being one in which a ratio of experienced people capable of generating the evaluation to a population needing screening is lower than in the remote geographic location.

16. The method of claim 15 wherein each raw image data file includes images of cells, and the method further includes, prior to electronic transmission of the remaining files, processing the remaining files to select for transmission images of cells which are most likely to result in a positive medical interpretation.

17. The method of claim 15 wherein the experienced person comprises a cytotechnologist or cytopathologist.

18. The method of claim 15 wherein the transmitting and receiving steps are performed via the Internet.

19. The method of claim 15 wherein the transmitting and receiving steps are performed via email.

20. The method of claim 15 further comprising preparing the Pap smears using a liquid-based thin-film sample preparation process.

21. The method of claim 20 wherein the preparing step is performed using an automated system.

22. The method of claim 15 wherein the remaining slides represent less than 50% of the Pap smear slides.

* * * * *